(12) United States Patent
Li et al.

(10) Patent No.: US 10,155,993 B2
(45) Date of Patent: Dec. 18, 2018

(54) METHOD OR KIT FOR DETERMINING LUNG CANCER DEVELOPMENT

(71) Applicant: National Taiwan University, Taipei (TW)

(72) Inventors: Ker-Chau Li, Taipei (TW);
Bing-Ching Ho, Taipei (TW);
Sung-Liang Yu, Taipei (TW);
Gee-Chen Chang, Taichung (TW);
Hsuan-Yu Chen, Taipei (TW);
Pan-Chyr Yang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/272,442

(22) Filed: Sep. 22, 2016

(65) Prior Publication Data
US 2017/0081727 A1  Mar. 23, 2017

Related U.S. Application Data

(60) Provisional application No. 62/222,194, filed on Sep. 22, 2015.

(51) Int. Cl.
*C12Q 1/6886* (2018.01)
*C12Q 1/68* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

PUBLICATIONS

Chen (J Clin Oncology, 2015, vol. 33, pp. 2303-2310).*
Ionnidis (Plost Med, 2005, 2(8):e124, pp. 696-701).*
Hegele (Arterioscler. Thromb. Vasc. Biol. 2002 22:1058-1061).*

* cited by examiner

*Primary Examiner* — Sarae L Bausch

(57) ABSTRACT

Disclosed herein is a method of determining whether a subject having or is at risk of developing lung cancer. The presence of the SNP locus of rs193100333, which corresponds to a mutation on YAP1 protein with a substitution of an arginine to a tryptophan at position 331, indicates the subject has or is at risk of developing lung cancer. Accordingly, also disclosed herein is a kit for facilitating the detection of the SNP locus of rs193100333.

5 Claims, 4 Drawing Sheets
Specification includes a Sequence Listing.

METHOD OR KIT FOR DETERMINING LUNG CANCER DEVELOPMENT

BACKGROUND OF THE INVENTION

1. Field of the Invention

The present disclosure in general relates to the field of cancer development. More particularly, the present disclosure relates to a method or a kit for making risk evaluation of lung cancer in a subject.

2. Description of Related Art

DNA is approximately 99.9% identical from one individual to the next. It is this 0.1% difference that confers a unique phenotype to each individual. In addition to being responsible for phenotypic variation, this "minor" variation among individuals is also associated with the development of diseases. Many scientists have begun to associate the risk of developing certain disease with the inheritance of specific variants, or single nucleotide polymorphisms (SNPs). SNP is a site where a single base substitution occurs at a frequency of at least 1% in the population, and the average occurrence of SNP in the human genome is about one out of every 1,900 base pairs.

Several SNPs are known to be correlated with the development of cancers. For example, SNP of rs4444903, which is located within epidermal growth factor (EGF) gene, might cause gallbladder and liver cancer; SNPs of rs1799950 and rs1799954, which are respectively located within breast cancer 1 (BRCA1) gene and BRCA2 gene, show correlation with breast cancer; SNP of rs2333227, which is located within myeloperoxidase (MPO) gene, might result in gastric and lung cancer; and SNP of rs3218536, which is located within X-ray repair cross complementing 2 (XRCC2) gene, likely plays a role in the development of breast and ovarian cancer.

Yes-associated protein 1 (YAP1), also known as YAP or YAP165, is encoded by YAP1 gene located in the human chromosome 11q22. As a multifunctional intra-cellular junctional protein and transcriptional co-activator, the aberrant expression of YAP1 might de-regulate cellular signal transduction and thus, result in the development of various diseases. Several types of cancers have been demonstrated to be related to the abnormal expression of YAP1. For example, overexpression of YAP1 was observed in several human cancers, including liver cancer, esophageal squamous cell carcinoma, non-small cell lung cancer, and ovarian cancer. Inappropriate expression of YAP1 in nuclear and cytoplasmic was associated with the occurrence of colonic adenocarcinoma, lung adenocarcinoma, and ovarian serous cystadenocarcinoma. Furthermore, even a single S127A mutation of YAP1 is shown to possess the capability of enhancing mammary carcinoma and melanoma growth and promoting their metastasis. Therefore, the abnormal expression of YAP1 protein is in a close relationship with oncology.

Lung cancer is the most common cause of cancer-related death in men and women, and is responsible for about 1-2 million deaths worldwide annually. However, current risk evaluation of lung cancer based on genome typing and/or protein expression is still poor in accuracy, nor is it efficient either. Thus, there exists a need in the related art for a more accurate and efficient method for making risk assessment on a subject whether he/she has or is at risk of developing lung cancer.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, disclosure herein features a method of making a risk assessment to a subject whether he/she has or is at risk of developing lung cancer; and accordingly, a kit that facilitates the risk evaluation.

One aspect of the present disclosure pertains to a method of determining whether a subject has or is at risk of developing lung cancer. The method comprises obtaining a biological sample from the subject, extracting DNA from the biological sample, and detecting the presence or absence of a SNP locus of rs193100333 in the extracted DNA, wherein the presence of the SNP locus of rs193100333 indicates the subject has or is at risk of developing lung cancer.

According to some embodiments of the present disclosure, the method further comprises amplifying the extracted DNA by use of a pair of primers respectively having the nucleotide sequences of SEQ ID NOs: 1 and 2.

According to some embodiments of the present disclosure, the SNP locus is detected by an assay selected from the group consisting of direct sequencing, primer extension, dynamic allele-specific hybridization (DASH), molecular beacons, SNP microarrays, restriction fragment length polymorphism (RFLP), quantitative polymerase chain reaction (qPCR), flap endonuclease (FEN), single strand conformation polymorphism, temperature gradient gel electrophoresis (TGGE), denaturing high performance liquid chromatography (DHPLC), high-resolution melting of the entire amplicon, and DNA mismatch-binding proteins. In the embodiments of the present disclosure, the SNP locus is detected by the primer extension assay, which is achieved by matrix assisted laser desorption ionization time-of-flight mass spectrometry (MALDI-TOF MS).

According to some embodiments of the present disclosure, the biological sample is any of a skin biopsy sample, a whole blood sample, a buffy coat sample, a plasma sample, a serum sample, a urine sample, or a mucus sample.

According to the embodiments of the present disclosure, the subject is a Chinese.

According to some embodiments of the present disclosure, the SNP locus of rs193100333 corresponds to a mutation on YAP1 protein with a substitution of an arginine to a tryptophan at position 331.

Another aspect of the present disclosure pertains to a kit for facilitating the detection of a SNP locus of rs193100333 in a biological sample of a subject for determining whether the subject has or is at risk of developing lung cancer. The kit comprises a pair of primers, which respectively have the nucleotide sequences of SEQ ID NOs: 1 and 2 for use in a PCR reaction for amplifying a DNA segment that contains the SNP locus of rs193100333 in the biological sample; and PCR reaction reagents, which comprises PCR reaction enzymes, $MgCl_2$, deoxynucleotide triphosphates (dNTPs), PCR reaction buffer, and double-distilled water.

In certain embodiments of the present disclosure, the kit further comprises a DNA template that has a SNP locus of rs193100333 within its nucleotide sequence as a positive control. In other embodiments of the present disclosure, the kit further comprises a DNA template that lacks a SNP locus of rs193100333 within its nucleotide sequence as a negative control.

Many of the attendant features and advantages of the present disclosure will become better understood with reference to the following detail description.

BRIEF DESCRIPTION OF THE DRAWINGS

The present description will be better understood from the following detailed description read in light of the accompanying drawings, where.

DETAILED DESCRIPTION OF THE INVENTION

Figure 1A:
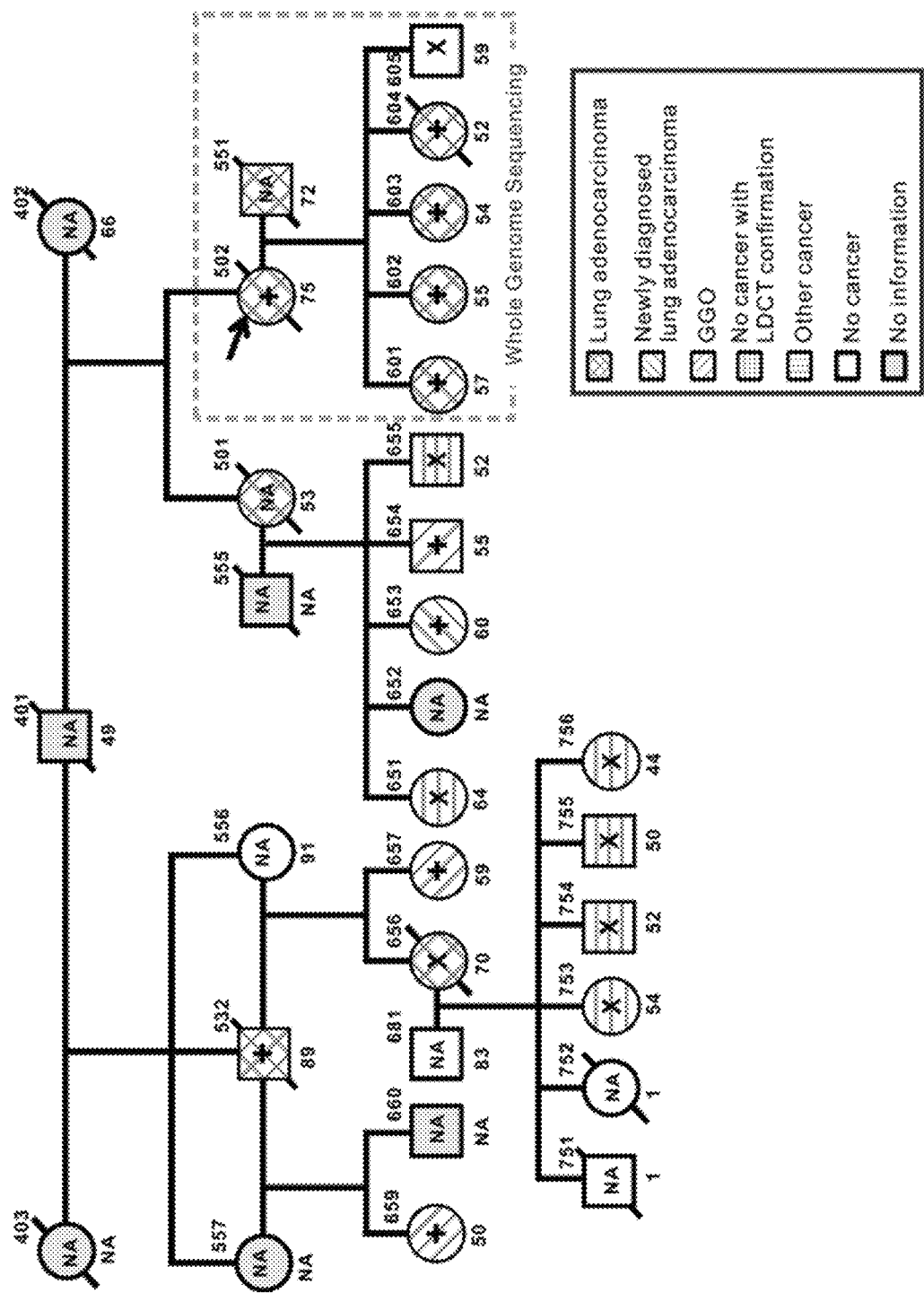
FIGS. 1A and 1B are pedigrees of the original family (FIG. 1A) and the validation cohort (FIG. 1B), in which the probands were indicated by the arrows; shape symbols indicated gender: square for male and circle for female; +, x, and NA inside the shape symbol indicated YAP1 R331W carrier, non-carrier, and DNA not available, respectively; deceased subjects were indicated by slashes through the shape symbols; colors indicated subjects' health statuses: lung adenocarcinoma in red, newly diagnosed lung adenocarcinoma in peach, ground glass opacity (GGO) in blue, no cancer with low dose computed tomography (LDCT) confirmation in green, other cancers in purple, normal status in white, and unknown status in grey; ages were shown under the symbols; in according to the examples of the present disclosure.

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

As used herein, the term "single nucleotide polymorphism (SNP)" refers to a DNA sequence variation occurring when a single nucleotide—A, T, C, or G—in the genome (or other shared sequence) differs between members of a species (or between paired chromosomes in an individual). In general, each SNP is assigned with a reference SNP ID (rs) in Single Nucleotide Polymorphism Database (db SNP) hosted by the National Center for Biotechnology Information (NCBI) collaboration with National Human Genome Research Institute (NHGRI).

"Nucleotide sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "subject" refers to any mammal, including the human species, which may benefit from the method of the present disclosure. Further, the term "subject" intends to refer to both the male and female gender unless one gender is specifically indicated. According to preferred embodiments of the present disclosure, the subject is a Chinese.

The practices of this invention are hereinafter described in detail with respect to a method of making a risk evaluation by detecting the SNP locus of rs193100333 so as to evaluate the development of lung cancer in a subject; and accordingly, a kit for facilitating the detection of the SNP locus of rs193100333.

One aspect of the present disclosure is directed to a method of determining whether a subject has or is at risk of developing lung cancer. The method comprises steps of, obtaining a biological sample from the subject; extracting DNA from the biological sample; and detecting the presence or absence of a SNP locus of rs193100333 in the extracted DNA; wherein the presence of the SNP locus of rs193100333 indicates that the subject has or is at risk of developing lung cancer. According to some embodiments of the present disclosure, the method further comprises amplifying the extracted DNA by use of a pair of primers respectively having the nucleotide sequences of SEQ ID NOs: 1 and 2. The pair of primers are used in a PCR reaction and specifically amplify a DNA segment containing the SNP locus of rs193100333. The DNA amplification would facilitate the subsequent detection of SNP locus of rs193100333, and enhances the accuracy of the risk evaluation rendered by the present method.

According to the embodiments of the present disclosure, the SNP locus of rs193100333 is detected by an assay selected from the group consisting of direct sequencing, primer extension, dynamic allele-specific hybridization (DASH), molecular beacons, SNP microarrays, restriction fragment length polymorphism (RFLP), quantitative polymerase chain reaction (qPCR), flap endonuclease (FEN), single strand conformation polymorphism, temperature gradient gel electrophoresis (TGGE), denaturing high performance liquid chromatography (DHPLC), high-resolution melting of the entire amplicon, and DNA mismatch-binding proteins.

In one embodiment of the present disclosure, direct sequencing of the whole genome is used to detect the SNP locus of rs193100333. The whole genome sequencing may be achieved by use of the next generation sequencing (NGS) assay. In NGS, a single genomic DNA is first fragmented into a library of small segments that can be uniformly and accurately sequenced in millions of parallel reactions. The newly identified strings of bases, called reads, are then reassembled using a known reference genome as a scaffold (resequencing), or in the absence of a reference genome (de novo sequencing). The full set of aligned reads would reveal the entire sequence of each chromosome of the genomic DNA.

In another embodiment of the present disclosure, primer extension assay is used to detect the SNP locus of rs193100333. The primer extension assay may be achieved by use of Matrix assisted laser desorption ionization time-of-flight mass spectrometry (MALDI-TOF MS). Mass spectrometry is an experimental technique used to identify the components of a heterogeneous collection of biomolecules, by sensitive discrimination of their molecular masses. In MALTI-TOF MS, the sample to be analyzed is placed in a UV-absorbing matrix pad and exposed to a short laser pulse. The ionized molecules are accelerated off the matrix pad (i.e., desorption) and move into an electric field towards a detector. The "time of flight" required to reach the detector depends on the mass/charge (m/z) ratio of the individual molecules. To use MALTI-TOF MS for DNA sequencing, the DNA sequence to be sampled is first transcribed into RNA in vitro in 4 separate reactions, each with three rNTP bases and one specific dNTP. The incorporated dNTP in the transcribed RNA will prevent cleavage from occurring at that dNTP position by RNAse, and therefore generate distinct fragments. Each fragment has a characteristic m/z ratio that appears as a peak in MALTI-TOF spectrum. The MALTI-TOF mass signal pattern obtained for the DNA sample is then compared with the expected m/z spectrum of the reference sequence, which includes the products of all 4 cleavage reactions. Any SNP differences between the sample DNA and the reference DNA sequences will produce predictable shifts in the spectrum, and their exact nature can be deduced.

In still another embodiment of the present disclosure, quantitative polymerase chain reaction (qPCR) is used to detect the desired SNP locus. In qPCR, DNA sample that includes the SNP locus is amplified and simultaneously detected and quantitated with different primer sets that target each allele separately. Well-designed primers will amplify their target SNP at a much earlier cycle than the other SNPs. This allows more than two alleles to be distinguished, although an individual qPCR reaction is required for each SNP. To achieve high enough specificity, the primer sequence may require placement of an artificial mismatch near its 3'-end, which is an approach generally known as Taq-MAMA. This artificial mismatch induces a much greater amplification delay for non-target alleles than a single mismatch would alone, yet does not substantially affect amplification of the target SNP.

In still another embodiment of the present disclosure, the SNP locus is detected by direct sequencing of a specified DNA segment containing the SNP locus of rs193100333.

According to the embodiments of the present disclosure, the biological sample is any of a skin biopsy sample, a whole blood sample, a buffy coat sample, a plasma sample, a serum sample, a urine sample, or a mucus sample. Preferably, the biological sample is a whole blood sample; more preferably, white blood cells and platelets obtained from the whole blood sample.

According to the embodiments of the present disclosure, the SNP locus of rs193100333 corresponds to a mutation on YAP1 protein with a substitution of an arginine to a tryptophan at position 331.

Another aspect of the present disclosure is directed to a kit for facilitating the detection of the SNP locus of rs193100333 in a biological sample of a subject for determining whether the subject has or is at risk of developing lung cancer. The kit comprises a pair of primers; PCR reaction reagents; and an instruction, which provides guidance to the user in how to use the kit. The pair of primers respectively have the nucleotide sequences of SEQ ID NOs: 1 and 2 for use in a PCR reaction for amplifying a DNA segment containing the SNP locus of rs193100333 in the biological sample. The PCR reaction reagents comprise PCR reaction enzymes, $MgCl_2$, deoxynucleotide triphosphates (dNTPs), PCR reaction buffer, and double-distilled water.

According to some embodiments of the present disclosure, the kit further comprises a DNA template that has a SNP locus of rs193100333 within its nucleotide sequence as a positive control. According to other embodiments of the present disclosure, the kit further comprises a DNA template that lacks a SNP locus of rs193100333 within its nucleotide sequence as a negative control.

The present disclosure provides a correlation between the SNP locus of rs193100333 and the occurrence of lung cancer. The following examples illustrate the method of determining whether a subject has or is at risk of developing lung cancer and a kit that facilitate the risk evaluation. The examples are illustrative only, and do not limit the scope of the present invention.

EXAMPLE

Materials and Methods

Study Populations

Subjects of this study were drawn from two projects—Genetic Epidemiology Study of Lung Adenocarcinoma (GELAC) and Cancer Screening Project (CSP). The GELAC project recruited lung cancer patients, their relatives and matched healthy controls. The control subjects in GELAC were cancer-free individuals randomly selected from the health examination clinics of the same hospitals during the same time period of case recruitment. For this study, all lung cancers were adenocarcinoma and all the genomic DNAs of the patients and their relatives were collected in GELAC. The Cancer Screening Project (CSP) was a community based prospective study with healthy subjects enrolled from seven townships in Taiwan.

To validate the SNP correlated with lung cancer, one family with 6 lung cancer patients was selected from the GELAC project, and their genome was screened and analyzed by whole genome sequencing. The mother and her 4 daughters of the family were diagnosed with lung adenocarcinoma, while the son was healthy. The father also died of lung adenocarcinoma but his DNA was not available. All 6 lung cancer patients were without smoking history.

After the screening, 30 normal subjects were selected from the CSP for the MALDI-TOF assay so as to eliminate the SNPs expressed in healthy subjects.

Further, 1135 normal control subjects and 1312 lung cancer patients were recruited to verify the correlation between the SNP YAP1 R331W and lung cancer. All lung cancer cases were drawn from the GELAC project. In the 1135 healthy subjects, 470 subjects were from the CSP and 665 subjects were from the GELAC project.

The genomic DNA was extracted from the buffy coat of peripheral blood in each sample followed by standard protocol, respectively. This investigation was performed after approval by the Institutional Review Board. Written informed consent was obtained from all patients.

Genotyping by Next Generation Sequencing (NGS) Assay

Mate-paired libraries were generated for the SOLiD™ 4 System according to the manufacturer's standard protocol (Life Technologies, Foster City, Calif.). In brief, genomic DNA was sheared into about 3 kb fragments for library preparation, which was then used as templates for emulsion PCR. Library fragments were coupled to beads via an adapter sequence and clonally amplified using the SOLiD™ EZ Bead™ Systems (Life Technologies, Foster City, Calif.). The amplified beads were then modified at the 3' end of DNA fragments to allow the beads to covalent attached to a slide. SOLiD™ sequencing primers were hybridized to the adapter sequence and four fluorescently labeled di-base probes were used in ligation-based sequencing. Each nucleotide is sequenced twice in two different ligation reactions, which has been shown to increase the accuracy of sequencing. Fifty base pairs were sequenced for both forward (F3) and reverse (R3) tags. Sequencing data were mapped to the human genome reference sequence (hg19) using the SOLiD™ BioScope™ software pipeline according to the manufacturer's instruction.

Genotyping by Matrix Assisted Laser Desorption Ionization Time-of-Flight Mass Spectrometry (MALDI-TOF MS)

MALDI-TOF MS by using MassARRAY system (SEQUENOM, San Diego, Calif.) was used to confirm genomic variations detected from NGS assay, according to the previous report for SNP genotyping setup by Su K-Y et al. (Pretreatment Epidermal Growth Factor Receptor (EGFR) T790M Mutation Predicts Shorter EGFR Tyrosine Kinase Inhibitor Response Duration in Patients With Non-Small-Cell Lung Cancer, Journal of Clinical Oncology, 30:433-440, 2012).

Genotyping by Quantitative Polymerase Chain Reaction (qPCR) Assay

TaqMan based qPCR assay (Life Technologies, Carlsbad, Calif.) was used for genotyping YAP1 R331W allele according to the manufacturer's instruction.

Genotyping Toward the Specified DNA Segment

The specified DNA segment and libraries construction were carried out by Pacific Biosciences (Pacific Biosciences, Menlo Park, Calif.) according to the manufacturer's instruction. For 5 kb insert library construction, 200 ng genomic DNAs were applied to PCR amplification with a pair of primers respectively having the nucleotide sequences of SEQ ID NO: 1 (located at −594 bp) and SEQ ID NO: 2 (located at +4612 bp, while the YAP1 rs193100333 is designated as +1). The amplified DNA segments were purified, end repaired, and ligated with SMRTbell sequencing adapters. The resulting sequencing libraries were purified three times using 0.6× volumes of Agencourt AMPure XP beads (Beckman Coulter Genomics, Denver, Colo.). SMRTbell sequencing libraries were mixed with sequencing primer and polymerase and subjected to Pacific Biosciences sequencing on the PacBio RS instrument with 120-min sequencing period followed by primary data analysis (Pacific Biosciences, Menlo Park, Calif.). All libraries were sequenced using v.2 chemistry and v.1.3.3 analysis software (Pacific Biosciences, Menlo Park, Calif.) according to the manufacturer's instruction.

Bioinformatic Analysis

The standard SOLiD software BioScope (Life Technologies, Foster City, Calif.) was carried out to analyze sequencing data including image analysis, mapping to human reference genome (UCSC Hg19), and single nucleotide mutation detection. SIFT software was performed to annotate the detected genomic variations.

Four steps of selection for discovering risk alleles were involved in this invention. The first step incorporated the hereditary relationship between the members of the family with 6 lung cancer patients selected from the GELAC project as described in Study Populations section. As father (DNA not available), mother, and 4 daughters were lung adenocarcinoma patients and the son was not affected, it is speculated that at least one of the parents must have a risk allele and transmitted it to the affected daughters and no risk allele was transmitted to son. Hence, daughters may have heterozygous or homozygous risk alleles. Mutations detected from NGS that met the transmission specification were selected.

The second step of selection used MALDI-TOF MS data. Only the non-synonymous mutations derived from the first step of selection were subjected to confirmation by MALDI-TOF MS platform.

After excluding the incorrect genotypes found by MALDI-TOF MS, the third step of selection was to compare the remaining candidate list with the published 4 individual genomes including YH1, Korean, Watson, and Venter. Mutations from any of these 4 individual genomes were excluded.

In the final step of selection, since it is assumed that disease-causing alleles should have low allele frequency in Taiwan, candidate mutations were genotyped by MALDI-TOF MS in 30 normal persons from the CSP. The mutations detected in anyone of the 30 normal were further excluded from the candidate list to make sure that disease candidate mutations were rare in other non-affected individuals. A total of 1312 lung adenocarcinoma patients and 1135 normal subjects were collected to validate the findings of this study in two steps. In the first validation step, after 4 steps of candidate allele selection, the remaining candidate mutations were genotyped validated in the cohort of 1135 normal persons and 651 lung adenocarcinomas by MALDI-TOF MS. In the second step, only significant risk alleles form the first step will be genotyped by TaqMan based qPCR.

Colony Formation Assay

To determine the ability of cells to grow in an anchorage-independent manner, the bottom layer of 6-well plates contained 0.7% agarose in PBS, while the top layer contained 0.3% agarose in medium with 10% FBS. A549 lung cancer cells were suspended in 1 ml RPMI containing 0.35% low-melting point agarose and seeded onto the top layer at the density of $2\times10^3$ cells/well. After 3 weeks, the wells were washed in PBS, fixed in 4% paraformaldehyde, and stained with 0.1% crystal violet. Finally, colonies greater than 0.5 mm were counted in three independent experiments.

Matrigel Invasion Assay

The invasion ability of cells was evaluated using Boyden chamber, which consists of two medium-filled compartments (i.e., upper and lower compartments) separated by a micro-porous polycarbonate membrane. The polycarbonate membrane having 8-um pores (Costar, Cambridge, Mass.) was coated with Matrigel (Becton Dickinson, Franklin Lakes, N.J.) and inserted between the two compartments. $1\times10^4$ A549 lung cancer cells were seeded onto upper compartment of the chamber (which was filled with 200 uL serum free medium) and allowed to migrate through the pores of the membrane and into the lower compartment (which was filled with a medium containing 10% FBS). After 16 hours incubation, the cells invaded across the Matrigel coated membrane were fixed with methanol, and stained with Giemsa solution (Sigma, St Louis, Mo.). The cells in the lower compartment were counted under a light microscope at 200× magnification. The experiment was performed in triplicate.

Statistical Analysis

Fisher's exact test was performed to test the difference of frequencies between groups. The multivariate logistic regression with covariates of age, gender, and smoking status was used to estimate the risk magnitude of risk alleles. Statistical analysis was conducted by SAS 8 (SAS Institute Inc., Cary, N.C.). All tests were two-tailed and p values<0.05 were considered significant.

Example 1 Identification of YAP1 R331W Mutation in Subjects Having Lung Cancer 1.1 Genotyping and Validation of YAP1 R331W To verify the correlation between SNP and lung cancer, whole genome sequencing was conducted on a high-density lung adenocarcinoma family (hereinafter "original family") selected from the GELAC project described above, wherein the mother (NO: 502, indicated by the arrow) and her four daughters (NOs: 601-604) all have lung cancers, whereas her son (NO: 605) does not (FIG. 1A). The average throughput of NGS assay is around 73 Gb with 24× coverage. Around 3 million single nucleotide mutations were detected per person by the NGS assay (Table 1).

TABLE 1

Summary of sequencing data for members of lung adenocarcinoma family

|  | M | S | D1 | D2 | D3 | D4 |
|---|---|---|---|---|---|---|
| Throughput (Gb) | 78 | 85 | 51 | 79 | 64 | 83 |
| Average coverage | 25X | 28X | 17X | 25X | 21X | 27X |
| single nucleotide mutation | 3,257,689 | 3,247,294 | 2,782,421 | 3,233,849 | 3,148,046 | 3,272,729 |

M, S, and D1 to D4 denoted mother, son, and 4 daughters, respectively.

To compare the difference between subjects with or without lung cancer, the dominant model was performed and there were 70,827 SNPs detected on the mother and her four daughters, but not on her son. From these detected SNPs, 240 non-synonymous alleles were identified.

These 240 alleles were further genotyped on another 30 normal Chinese subjects, selected from the Cancer Screening Project (CSP) described above, by MALDI-TOF to eliminate all SNPs found from the normal subjects. Only 6 alleles remained after the screen and one of them is located on chromosome 11q, the exon 6 of YAP1 gene. This SNP with a reference SNP ID of rs193100333 corresponds to a mutation on YAP1 protein, in which arginine was substituted to tryptophan at position 331.

Next, for validation of YAP1 R331W in subjects having lung cancers, a cohort of 1312 lung adenocarcinomas (hereinafter "validation cohort") and 1135 normal subjects were respectively analyzed by genotyping with MALDI-TOF MS assay and qPCR assay. As illustrated in Table 2, the low YAP1 R331W frequency in normal subjects (0.18%) is consistent with the number reported in the Asian population of the 1,000 genome project (1 out of 286 or 0.35%, data not shown). Meanwhile, for the lung adenocarcinomas subjects, 1.1% (p=0.0095) increase in the mutant carrier frequency was found with an odd ratio (OR) of 6.1. After adjusting for the age, smoking history, and gender variations, an adjusted OR of 5.9 (p=0.019) was obtained (Table 3). This ratio is much higher than that reported in well-known genome-wide lung cancer studies, in which the odds ratio is <2.0.

TABLE 2

Frequency distribution of YAP1 R331W carriers

|  | Normal control | Lung adenocarcinoma | | | P value |
|---|---|---|---|---|---|
|  |  | MALDI-TOF | PCR | Total |  |
| Sample size | 1135 | 651 | 661 | 1312 | 0.0095[†] |
| Carrier number (%)* | 2 (0.18%) | 8 (1.2%) | 6 (0.9%) | 14 (1.1%) |  |

[†]Comparison of carrier frequency between lung adenocarcinoma (total) and normal control by Fisher's exact test.
*All carriers were heterozygous carriers.

TABLE 3

Risk analysis of YAP1 by multivariate logistic regression. All carriers were heterozygous and the dominant genetic model was used.

| Variable | Odds ratio* | 95% CI | P value |
|---|---|---|---|
| YAP1 R331W | 5.91 | 1.33-26.33 | 0.019 |
| Age | 1.02 | 1.01-1.03 | <0.0001 |

TABLE 3-continued

Risk analysis of YAP1 by multivariate logistic regression. All carriers were heterozygous and the dominant genetic model was used.

| Variable | Odds ratio* | 95% CI | P value |
|---|---|---|---|
| Gender | 0.39 | 0.31-0.48 | <0.0001 |
| Smoking | 2.26 | 1.79-2.86 | <0.0001 |

*adjusted odds ratio
CI: confidence interval

The data indicated that YAP1 R331W mutation might be a potential marker for the risk evaluation of lung adenocarcinoma.

1.2 Pedigrees of Lung Adenocarcinoma Family
1.2.1 Pedigrees of Original Family

Since gene mutations and/or SNP locus are associated with inherited susceptibility to diseases (e.g., cancers), the YAP1 R331W was further traced over the relatives of the proband of the original family, in which the proband (NO: 502) is indicated by the arrow and the family covers four generations (FIG. 1A). All subjects with available DNA were tested for YAP1 mutation. The proband's father had two wives, thus the proband had one sister and three half-brothers, among them, two (NOs: 532 and 501) were identified to have lung adenocarcinoma. Subject 532 was identified to carry the YAP1 mutation, whereas the DNA sample of subject 501 was unavailable. However, inferring from the YAP1 inheritance pattern, subject NO: 501 should also be a mutant carrier.

Subject NO: 501 had five children. Among the four with available DNA, two were tested positive (NOs: 653 and 654), and both of them were contacted for low dose computed tomography (LDCT) scanning. Subject NO: 653, a non-smoker, a positive LDCT result eventually led to an operation on stage I lung adenocarcinoma. As to Subject NO: 654, a pulmonary ground-glass opacity (GGO) lesion about 8 mm in size over RUL (right upper lobe) in lung was identified, and she is still under monitoring. The two non-carriers (NOs: 651 and 655) were found negative on lung lesions.

Subject NO: 532 (deceased) had three children, and their genomic DNAs were available for subsequent studies (NOs: 656, 657, and 659). Subject NO: 656 had lung adenocarcinoma while carrying YAP1 wild-type, DNA from her four children (NOs: 753, 754, 755, and 756) were tested negative on YAP1 mutant and all are healthy. Subject NO: 657 carried YAP1 mutant, and her LDCT scan indicated 4 GGO lesions ranging from 4 to 8 mm in size over bilateral lungs three years ago, however, she failed to show up in follow-up visits of the present study. Subject NO: 659 also carried YAP1 mutant, and had a 5 mm GGO lesion over LLL (left lower lobe) of the lung.

1.2.2 Pedigrees of Validation Cohort

Figure 1B:
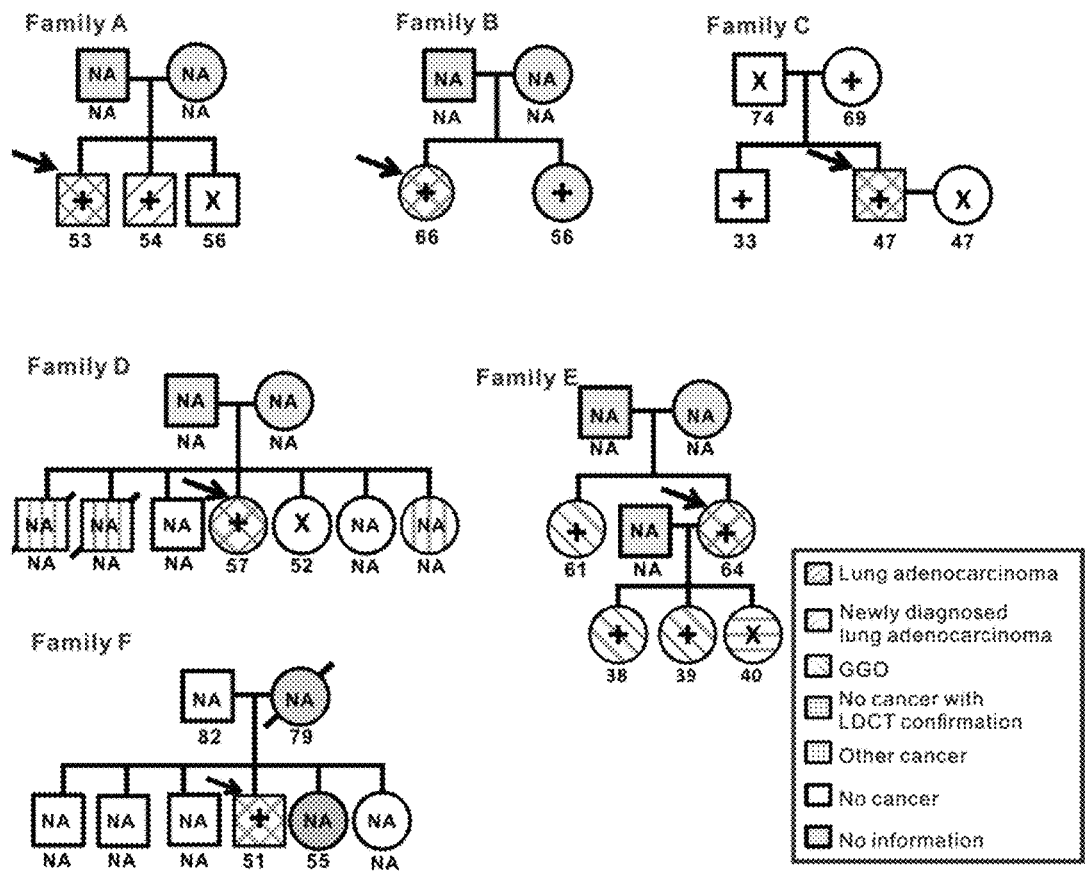

Among the validation cohort, 14 out of 1312 subjects having lung adenocarcinomas were found to carry YAP1 mutation. Six of them had family profiles available (FIG. 1B). The genomic DNA of their relatives collected was conducted YAP1 mutation test.

In family A, the proband's (NO: 53, indicated by the arrow) YAP1 mutant brother (NO: 54) was diagnosed with advanced lung adenocarcinoma 2 months before the contact was made.

In family E, all three YAP1 mutant carriers (NOs: 61, 38, and 39) have GGO lesions over their lungs based on LDCT scans (the sister has GGO lesion, 8 mm over LLL of lung; and the two daughters respectively have, GGO, 6 mm, RUL, and 5 mm, LLL of lungs). In contrast, LDCT of the wild-type daughter (NO: 40) showed no sign of GGO.

In family D, three siblings (colored in purple) of the proband (NO: 57, indicated by the arrow) had other cancers, but we were unable to obtain their DNA samples. Notably, the YAP1-mutant probands of families D and E respectively had breast cancers.

In view of above findings, the health status of members of the original multiplex family and six new carriers' families can be classified into lung adenocarcinoma, GGO, no cancer, and no updated health information. The results indicated that subject(s) with a YAP1 R331W mutation had an overwhelmingly high frequency of developing lung adenocarcinoma or GGO compared with subjects carrying a wild-type gene (10:0 versus 1:7; p=0.0003) (Table 4).

TABLE 4

Distribution of YAP1 R331W mutation among the LDCT-confirmed healthy subjects or subjects having lung adenocarcinoma or GGO

| YAP1 R331W | Lung adenocarcinoma | GGO | LDCT-confirmed no cancer | P value[†] | Others (no LDCT) |
|---|---|---|---|---|---|
| Mutant (n = 13)* | 4 | 6 | 0 | 0.0003 | 3 |
| Wild-type (n = 12) | 1 | 0 | 7 | | 4 |

*One mutant case was inferred from family genetic inherence pattern.
[†]Comparison of YAP1 R331W mutation status versus lung adenocarcinoma, GGO with LDCT confirmation, and no cancer with LDCT confirmation by Fisher exact test.

Taken together, the data suggested that YAP1 R331W mutation is closely correlated with the development of lung adenocarcinoma or GGO.

Example 2 Characterization of the Functional Relationship Between YAP1 R331W Mutation and Lung Adenocarcinoma or GGO Using YAP1 Mutant Cells Human lung adenocarcinoma cell line A549, which expresses wild-type YAP1, was used in this example for the investigation of the role of YAP1 R331W mutation in lung adenocarcinoma or GGO. For this purpose, the endogenous YAP1 expression was silenced by shRNA-YAP1 lentivirus that targets the 3'UTR of YAP1; as comparison, wild-type YAP1 and YAP1 R331W expression vectors were respectively transfected and overexpressed in YAP1-silenced A459 cells as well. Results were evaluated respectively by colony formation and cell invasion assays according to procedures set forth in the "Materials and Methods" section. Results are depicted in FIGS. 2A and 2B.

Figure 2A:
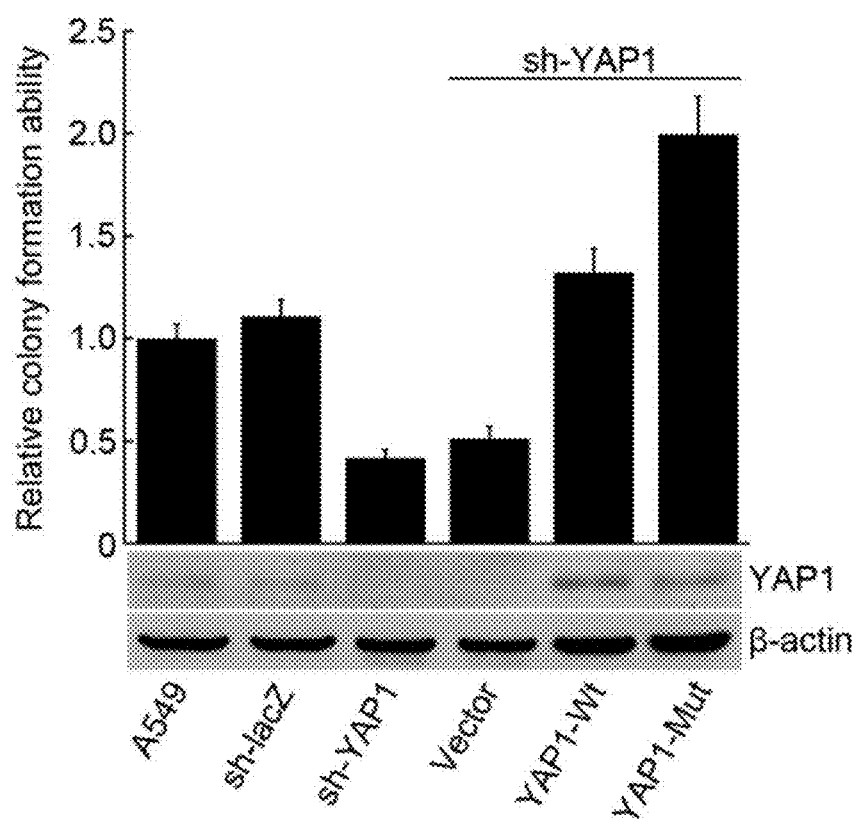
FIGS. 2A and 2B are histograms respectively depicting the colony formation ability (FIG. 2A) and the invasion ability (FIG. 2B) of specified cells; in according to the examples of the present disclosure.

As depicted in the western blot data of FIG. 2A, compared with the control groups (i.e., A549 or sh-lacZ), the expression of YAP protein was successfully down-regulated by the introduction of shRNA-YAP1 vector; whereas the expression of YAP1 could be restored by the overexpression of wild-type YAP1 or YAP1 R331W in YAP1 knockdown cells (i.e., YAP1-Wt or YAP1-Mut). Further, the introduction of YAP1 R331W mutation significantly increased the colony formation ability of YAP1 knockdown cells, even better than that of the control cells.

Figure 2B:
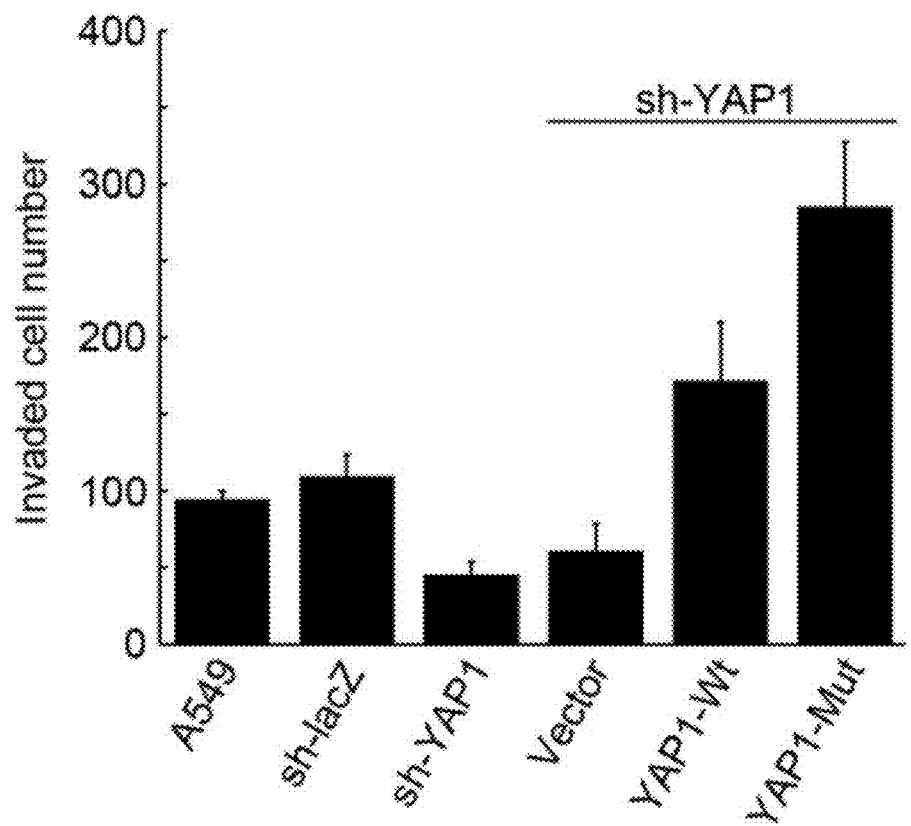

Results from the cell invasion assay as demonstrated in FIG. 2B indicated that cells that overly expressed YAP1 R331W (YAP1-Mut) exhibited the strongest invasion capability as compared with those of normal A549 cells, shRNA-lacZ knockdown cells (sh-lacZ), shRNA-YAP1 knockdown cells (sh-YAP1), YAP1 knockdown cells that overexpress vector control (Vector), and YAP1 knockdown cells that overexpress wild-type YAP1 (YAP1-Wt).

Taken together, introduction of YAP1 R331W mutation into the wild-type YAP1 protein would increase both the abilities of cells in terms of colony formation and invasion.

In sum, results from the foregoing working examples established that YAP1 R331W mutation might result in colony formation and invasion of cancer cells, which are consistent with the clinical data that YAP1 R331W mutation was inherited and closely correlated with the development of lung cancer. Accordingly, the YAP1 R331W point mutation may serve as a marker for making a risk evaluation on the development of lung cancer in a subject.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of determining whether a subject has increased risk of developing lung cancer, comprising:
   obtaining a biological sample from a human subject;
   extracting DNA from the biological sample;
   amplifying the extracted DNA by use of a pair of primers respectively having the nucleotide sequences of SEQ ID NOs: 1 and 2;
   detecting the presence of a single nucleotide polymorphism (SNP) at position rs193100333 in the extracted DNA corresponding to arginine to tryptophan mutation in the YAP1 protein at position 331; and
   determining the subject has increased risk of developing lung cancer;
   wherein the presence of the SNP rs193100333 indicates the subject is at increased risk of developing lung cancer.

2. The method of claim 1, wherein the SNP is detected by an assay selected from the group consisting of direct sequencing, primer extension, dynamic allele-specific hybridization (DASH), molecular beacons, SNP microarrays, restriction fragment length polymorphism (RFLP), quantitative polymerase chain reaction (qPCR), flap endonuclease (FEN), single strand conformation polymorphism, temperature gradient gel electrophoresis (TGGE), denaturing high performance liquid chromatography (DHPLC), high-resolution melting of the entire amplicon, and DNA mismatch-binding proteins.

3. The method of claim 2, wherein the primer extension assay is matrix assisted laser desorption ionization time-of-flight mass spectrometry (MALDI-TOF MS).

4. The method of claim 1, wherein the biological sample is any of a skin biopsy sample, a whole blood sample, a buffy coat sample, a plasma sample, a serum sample, a urine sample, or a mucus sample.

5. The method of claim 1, wherein the subject is Chinese.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: YAP1-F

```
<400> SEQUENCE: 1
ccaaagattt tcctaaat                                                18

<210> SEQ ID NO 2
<211> LENGTH: 23
<212> TYPE: DNA
<213> ORGANISM: Artificial Sequence
<220> FEATURE:
<223> OTHER INFORMATION: YAP1-R

<400> SEQUENCE: 2
acagcagtgt tgtttttatt tct                                          23
```